United States Patent [19]

Tomiyama et al.

[11] Patent Number: 5,175,184

[45] Date of Patent: Dec. 29, 1992

[54] BENZOTHIOPHENE DERIVATIVES AND ANTIHYPERURICEMIA THEREOF

[75] Inventors: Tsuyoshi Tomiyama, Sakaki; Akira Tomiyama, Togura; Koichi Kubota, Matsumoto, all of Japan

[73] Assignee: Kotobuki Seiyaku Company Limited, Sakaki, Japan

[21] Appl. No.: 870,106

[22] Filed: Apr. 17, 1992

Related U.S. Application Data

[60] Continuation of Ser. No. 665,663, Mar. 7, 1991, abandoned, which is a division of Ser. No. 280,564, Dec. 6, 1988, Pat. No. 5,004,750, which is a division of Ser. No. 891,276, Jul. 28, 1986, Pat. No. 4,797,415, which is a continuation-in-part of Ser. No. 543,292, Oct. 19, 1983, abandoned.

[30] Foreign Application Priority Data

Oct. 19, 1982 [JP] Japan ............................... 57-182130

[51] Int. Cl.$^5$ ................................ A61K 31/38
[52] U.S. Cl. ........................ 514/443; 514/382; 514/469; 549/57; 549/58; 549/462; 549/467
[58] Field of Search ................ 549/57, 58, 462, 467; 514/382, 443, 469

[56] References Cited

U.S. PATENT DOCUMENTS

| | | | |
|---|---|---|---|
| 4,007,204 | 2/1977 | Descamps et al. | 549/57 |
| 4,195,093 | 3/1980 | Laforest et al. | 514/443 |
| 4,255,585 | 3/1981 | Thullier et al. | 549/58 |
| 4,565,828 | 6/1986 | Descamps et al. | 514/469 |
| 4,797,415 | 1/1989 | Tomiyama et al. | 549/447 |
| 4,831,504 | 5/1989 | Levitt et al. | 514/469 |
| 5,004,750 | 2/1991 | Tomiyama et al. | 514/382 |
| 5,118,707 | 6/1992 | Chatterjee et al. | 514/469 |

FOREIGN PATENT DOCUMENTS

| | | | |
|---|---|---|---|
| 2279395 | 2/1976 | France | 514/443 |
| 2131795 | 6/1984 | United Kingdom | 549/57 |
| 89-02893 | 4/1989 | World Int. Prop. O. | 549/58 |

*Primary Examiner*—Donald G. Daus
*Attorney, Agent, or Firm*—Emmanuel J. Lobato; Robert E. Burns

[57] ABSTRACT

A new series of benzofuran and benzothiophene derivatives are disclosed. These compounds have a structure which can be obtained by substituting the third position of 2-lower alkyl-benzofuran or 2-lower alkyl-benzothiophene with a substituted benzene derivative, itaconic adic derivative or a substituted phenoxymethyl tetrazole derivative. They are useful as diuretics without side effects of elevating serum uric acid levels and can be used in the treatment of hyperuricemia.

8 Claims, No Drawings

BENZOTHIOPHENE DERIVATIVES AND ANTIHYPERURICEMIA THEREOF

This is a continuation of copending application Ser. No. 07/665,663, filed Mar. 7, 1991, now abandoned, which is a division of Ser. No. 07/280,564, filed Dec. 6, 1988, now U.S. Pat. No. 5,004,750, which is a division of Ser. No. 891,276, filed Jul. 28, 1986, now U.S. Pat. No. 4,797,415, which is a continuation-in-part of Ser. No. 543,292, filed Oct. 19, 1983 and abandoned.

BACKGROUND OF THE INVENTION

It is well known that hyperuricemia and hypertension are among major risk factors of cardiovascular diseases.

In long term diuretics therapy, for example, with the thiazide type diuretics, there occurs a frequent increase in serum uric acid levels. Such an increase leads to the occurrence of serious gouty arthritis.

The present invention relates to diuretics without the aforesaid side effect and discloses a series of chemical compounds effective in treating hyperuricemia.

SUMMARY OF THE INVENTION

The principal object of the present invention is to provide novel compounds having pharmaceutically effective properties.

Another object of the present invention is to provide pharmaceutical compositions useful as antihyperuricemia agents.

Still further important objects of the present invention are to provide benzofuran or benzothiophene derivatives and a method of manufacturing the same.

These and other objects of the present invention will become apparent from the following description.

DESCRIPTION OF THE INVENTION

This invention relates to a new series of benzofuran and benzothiophene derivatives, new antihyperuricemia agents, and a method of manufacturing the same.

The new compounds of the invention have the formula:

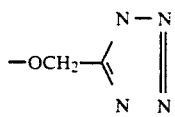

wherein,

A is oxygen or sulfur,
$R^1$ is lower alkyl,
Y is carbonyl, alkoxymethine, or hydroxymethine
B is

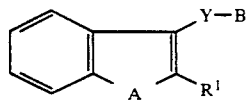 or 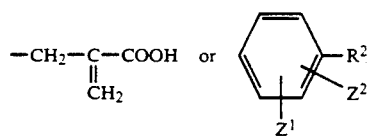

wherein $Z^1$ and $Z^2$ are each hydrogen, lower alkyl, halogen or a nitro group.

$R^2$ is hydroxy, —O—$(CHR^3{}_n)$—$COR^4$ wherein $R^3$ is hydrogen or lower alkyl; $R^4$ is hydroxy, alkoxy, amino, hydroxyamino, glycinamide residue or glycine ester residue and n is an integer having a value of 1 or 2 or $$-OCH_2-\!\!\!\begin{array}{c}N-N\\ \diagup\quad\;\;\|\\ \diagdown\quad\;\;\|\\ N\quad\;\;N\end{array}$$

and nontoxic, pharmaceutically acceptable addition salts thereof are included in this invention.

The above symbols and their definitions apply hereinafter, unless otherwise noted.

The compounds of the invention have strong uricosuric and diuretic activities, and therefore pharmaceutical compositions containing at least one of the compounds of formula I are useful in the treatment of hyperuricemia.

The term "lower alkyl" used herein refers to alkyl groups which contain from 1 to 4 carbon atoms.

The following compounds are of particular interest:
(1) 2-(2-ethyl-3-benzofuroyl)phenoxyacetic acid
(2) 3-(2-ethyl-3-benzofuroyl)phenoxyacetic acid
(3) 4-(2-ethyl-3-benzofuroyl)phenoxyacetic acid
(4) 4-(2-ethyl-3-benzofuroyl)phenoxypropionic acid
(5) 4-(2-ethyl-3-benzofuroyl)phenoxy 2-methylacetic acid
(6) Ethyl 4-(2-ethyl-3-benzofuroyl)phenoxyacetate
(7) 4-(2-ethyl-3-benzofuroyl)phenoxyacetamide
(8) 4-(2 ethyl-3-benzofuroyl)phenoxyacetohydroxamide
(9) Methyl 4-(2-ethyl-3-benzofuroyl)phenoxyacetoglycinate
(10) 4-(2-ethyl-3-benzofuroyl)phenoxyacetoglycinamide
(11) Methyl 4-(2-ethyl-3-benzofuroyl)phenoxyacetate
(12) (2-ethyl-3-benzofuranyl)-4-hydroxyphenylmethanol
(13) Ethyl 4-(2-ethyl-3-hydroxymethylbenzofuranyl)-phenoxyacetate
(14) Ethyl 4-(2-ethyl-3-ethoxymethylbenzofuranyl)-phenoxyacetate
(15) Butyl 4-(2-ethyl-3-bu,toxymethylbenzofuranyl)-phenoxyacetate
(16) 2-methyl-3-(4-hydroxybenzoyl)benxofuran
(17) Ethyl 4-(2-methyl-3-benxofuroyl)phenoxyacetate
(18) 4-(2-methyl-3-benzofuroyl)phenoxyacetic acid
(19) 2-ethyl-3-benzofuranyl 3-chloro-4-hydroxyphenyl ketone
(20) Ethyl 2-chloro-4- (2-ethyl-3-benzofuroyl)phenoxyacetate
(21) 2-methylene-4-oxo-4-(2-ethyl-3-benzofuranyl)-butyric acid--(
(22) 2-chloro-4-(2-ethyl-3-benzofuroyl)phenoxyacetic acid
(23) 2-ethyl-3-benzofuranyl 3-methyl-4-hydroxyphenyl ketone
(24) Ethyl 2-methyl-4-2-ethyl-3-benzofuroyl)phenoxyacetate
(25) 2-methyl-4-2-ethyl-3-benzofuroyl)phenoxyacetic acid
(26) 2-ethyl-3-benzofuranyl 3-nitro-4-hydroxyphenyl ketone
(27) Ethyl 2-nitro-4-(2-ethyl-3-benzofuroyl)phenoxyacetate
(28) 4-(2-ethyl-3-hydroxymethylbenzofuranyl)phenoxyacetamide
(29) 2-ethyl-3-(4-hydroxybenzoyl)thianaphthene
(30) Ethyl 4-(2-ethyl-3-benzothenoyl)phenoxyacetate

(31) 4-(2-ethyl-3-benzothenoyl)phenoxyacetic acid
(32) 2-ethyl-3-(2,3-dimethyl-4-hydroxybenzoyl)benzofuran
(33) Methyl 2,3-dimethyl-4-(2-ethyl-3-benzofuroyl)phenoxyacetate
(34) Ethyl 2,3-dimethyl-4-(2-ethyl-3-benzofuroyl)phenoxyacetate
(35) 2,3-dimethyl-4-(2-ethyl-3-benzofuroyl)phenoxyacetic acid
(36) 2-ethyl-3-(2,5-dimethyl-4-hydroxybenzoyl)benzofuran
(37) Methyl 2,5-dimethyl-4-(2-ethyl-3-benzofuroyl)phenoxyacetate
(38) Ethyl 2,5-dimethyl-4-(2-ethyl-3-benzofuroyl)phenoxyacetate
(39) 2,5-dimethyl-4-(2-methyl-3-benzofuroyl)phenoxyacetic acid
(40) 2-ethyl-3-(3,5-dimethyl-4-hydroxybenzoyl)benzofuran
(41) Ethyl 2,6-dimethyl-4-(2-ethyl-3-benzofuroyl)phenoxyacetate
(42) 2,6-dimethyl-4-(2-ethyl-3-benzofuroyl)phenoxyacetic acid
(43) 5-[4-(2-ethyl-3-benzofuroyl)phenoxymethyl]tetrazole
(44) 5-[2-chloro-4-(2-ethyl-3-benzofuroyl)phenoxymethyl]tetrazole
(45) 5-[2-methyl-4-(2-ethyl-3-benzofuroyl)phenoxymethyl]tetrazole
(46) [2,3-dimethyl-4-(2-ethyl-3-benzofuroyl)phenoxymethyl]tetrazole
(47) 5-[2,5-dimethyl-4-(2-ethyl-3-benzofuroyl)phenoxymethyl]tetrazole
(48) 5-[2,6-dimethyl-4-(2-ethyl-3-benzofuroyl)phenoxymethyl]tetrazole The above-mentioned compounds, 1 to 48, will be referred to, as Compound 1, Compound 2, . . . and Compound 42, respectively hereinafter.

The first step of the reaction sequence involves the reaction of 2-substituted benzofuran or benzothiophene (II):

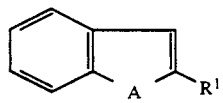

(II)

wherein the symbols are the same as in formula I with itaconic acid anhydride or its halogen activated derivatives.

To prepare another series of new compounds, 2-substituted benzofuran or benzothiophene (II) is reacted with anhydrous acid of the formula:

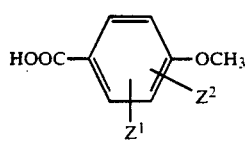

(III)

or with halogen activated derivatives of the formula III.

After demethylation of the reacted compound:

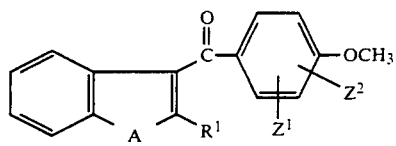

(IV)

wherein the symbols are the same as the formula I, and in case of need, after reduction of its carbonyl group to hydroxymethine, the resulting compound is caused to react with the compound of the formula:

$$X(CHR^3)_n-COR^4 \qquad (VI)$$

wherein X is a halogen atom and others are the same as formula I, the thus obtained compound is indicated as the formula I shown above. A more precise procedure of +he preparation of product of the present invention is shown hereinafter.

The first step of the reaction sequence involves the reaction of 2-substituted benzofuran or benzothiophene (II) with activated carbonic acid derivative (IIIa) in the presence of a Friedel-Crafts catalyst which yields the compound (IV).

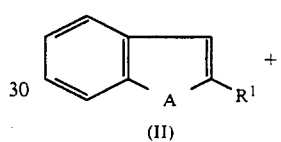

(II)

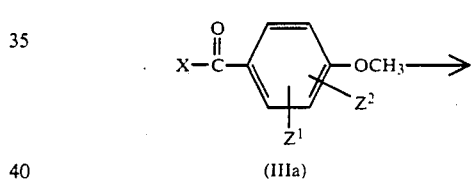

(IIIa)

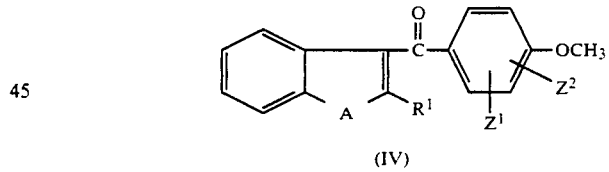

(IV)

The symbols are as previously shown.

After demethylation of the compound (IV), the resulting compound (V) is reacted with a compound shown as general formula (VI) in an aqueous solution or other solvent such as alcohol, tetrahydrofuran, dimethylformamide and toluene in the presence of a base, by heating to reflux in each solvent, or stirring at room temperature. The bases needed in this reaction are conventional ones such as sodium hydroxide or sodium ethoxide.

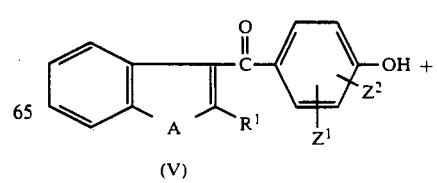

(V)

-continued

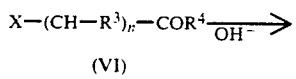

(VI)

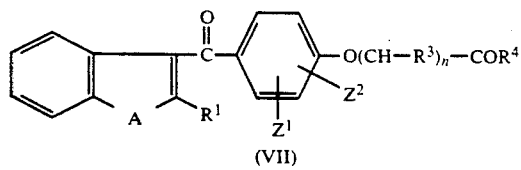

(VII)

The symbols are as shown hereinbefore.

Compound (VII) itself has sufficient hypouricemic activity.

In the formula (VII), if $R^4$ is methoxy or ethoxy, a compound shown in formula (VII) can be directly converted to an amide or hydroxyamide derivatives by treating the ester of formula (VII) with an amine or hydroxyamine.

In the formula (VII), if $R^4$ is an hydroxy group, a compound shown as formula (VII) is condensed with glycine to make a pro-drug by means of ordinary condensing agents such as diphenylphosphorylazide (DPPA) or dicyclohexylcarbodiimide (DCC). The carbonyl group in formula (V) can be easily reduced to a hydroxymethine group with $NaBH_4$. The hydroxymethine group can also be converted to an alkoxymethine group with a conventional alkylating agent such as alkyl halide in the presence of a base. The alkylhalides for use in this case will be enumerated as bromides and chlorides of alkyl having carbon atoms, of 1–4.

To prepare the compound shown in general formula I, in which B corresponds to

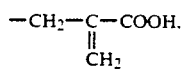

2-substituted compound III is reacted with anhydrous itaconic acid or halogen activated itaconic acid derivatves as shown below.

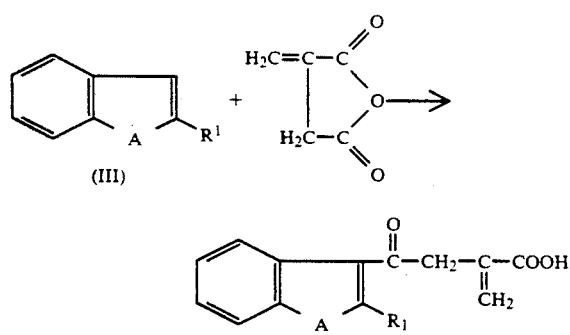

In the same manner as mentioned above, the carbonyl group of this compound can also be reduced to a hydroxymethine group and, if necessary, the hydroxymethine group is converted to an alkoxymethine group in the same manner.

To prepare the compounds shown in general formula (I), in which $R^2$ corresponds to

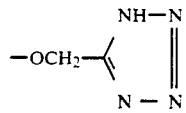

a compound shown as general formula (V) is condensed with $ClCH_2CN$ in the presence of sodium hydride. The resulting nitrile compound is converted to tetrazole (VIII) by $Al(N_2)_3$ as follows.

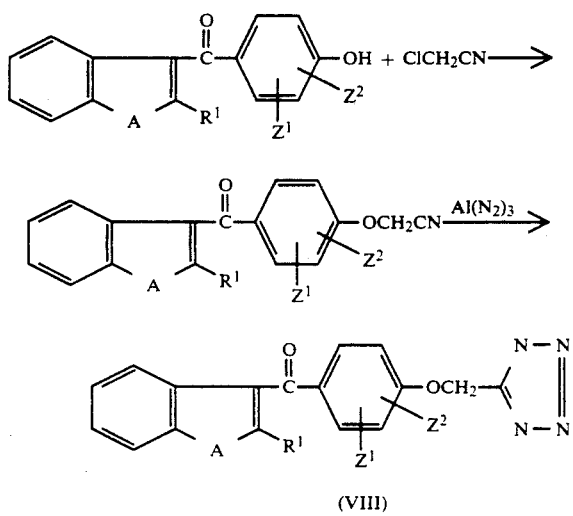

(VIII)

The symbols are as shown hereinbefore.

In general, the compounds related to this invention have a potent uricosuric activity and some of them are considered promising for clinical use. The toxicity of these compounds is much lower than that of the typical uricosuric agent: benzbromarone. For example, $LD_{50}$ of compound 3 is 2,110 mg/kg (p.o.) in mice, while that of benzbromarone is 361 mg/kg.

The route of administration of these compounds may be oral or parenteral but the oral route is preferred.

A wide variety of pharmaceutical forms can be employed, for example, such as tablets, granules and capsules in conventional dosages which should be determined clinically. These pharmaceutical preparations are made by the conventional techniques of the pharmaceutical and chemical art, such as by mxiing, granulating and compressing when necessary, or mixing and dissolving the ingredients in various ways appropriate to the desired end product.

The following examples will serve to illustrate the invention but are not intended to limit the scope of the invention.

Pharmacological Tests

A test compound was given to male mice weighing 18–28 g orally or subcutaneous at a dose of 200 mg/kg 30 minutes before 75 mg/kg phenol red injection via the caudal vein. Blood samples were collected from the retro-orbital plexus into heparinized capillary tubes 60 minutes after the phenol red injection. The retention of phenol red in circulation was determined according to the method described in J. Med. Pharmaceu. Chem. (1962) 5 p 175 which refers to the method of Kreppel, Med. exp. 1:285–289 (1959). The results which are-expressed in percentage of phenol red retention by comparison with the control group have been set forth in Table I.

TABLE I

| COMPOUND number | S. C. (200 mg/kg) (%) | P. O. (200 mg/kg) (%) |
| --- | --- | --- |
| 1 | 151.5 ± 15.2 | — |
| 2 | 180.3 ± 15.4 | — |
| 3 | 168.7 ± 18.1 | 175.0 ± 15.5 |
| 4 | 142.9 ± 19.0 | — |
| 5 | 158.1 ± 15.1 | 176.5 ± 17.6 |
| 6 | 207.2 ± 32.5 | 119.2 ± 2.3 |
| 7 | 123.1 ± 23.1 | 104.2 ± 8.3 |
| 8 | 167.0 ± 26.6 | 129.4 ± 17.6 |
| 9 | 125.0 ± 18.8 | 152.6 ± 15.8 |
| 10 | 123.1 ± 23.1 | 131.6 ± 26.3 |
| 11 | 114.2 ± 9.5 | — |
| 12 | 100.0 ± 21.4 | — |
| 13 | 114.3 ± 14.3 | — |
| 14 | 134.6 ± 34.6 | 120.0 ± 15.0 |
| 15 | 165.4 ± 34.6 | 175.0 ± 35.0 |
| 16 | 111.1 ± 11.1 | 112.5 ± 12.5 |
| 17 | 115.4 ± 19.2 | 105.0 ± 10.0 |
| 18 | 111.5 ± 15.4 | 135.0 ± 40.0 |
| 19 | 104.8 ± 19.0 | — |
| 20 | 127.7 ± 16.7 | — |
| 21 | 100.0 ± 13.6 | 165.2 ± 21.7 |
| 22 | 211.1 ± 33.3 | 189.5 ± 26.3 |
| 23 | 81.0 ± 14.3 | — |
| 24 | 172.2 ± 27.7 | — |
| 25 | 188.8 ± 27.8 | 200.0 ± 25.0 |
| 26 | 222.2 ± 27.7* | — |
| 27 | 111.1 ± 11.1 | — |
| 28 | — | — |
| 29 | 100.0 ± 21.4 | — |
| 30 | 85.7 ± 14.3 | — |
| 31 | 144.4 ± 22.2 | 162.5 ± 31.3 |
| 32 | — | 112.5 ± 18.8 |
| 33 | — | 133.4 ± 15.6 |
| 34 | — | 123.8 ± 28.6 |
| 35 | — | 319.0 ± 14.3 |
| 36 | — | 131.1 ± 15.6 |
| 37 | — | 253.5 ± 15.6 |
| 38 | — | 323.8 ± 19.0 |
| 39 | — | 409.5 ± 28.6 |
| 40 | — | 183.3 ± 22.2 |
| 41 | — | 183.3 ± 27.8 |
| 42 | — | 394.4 ± 44.4 |
| 43 | — | 430.0 ± 80.0 |
| 44 | — | 175.0 ± 17.9 |
| 45 | — | 217.9 ± 21.4 |
| 46 | — | 240.0 ± 64.0 |
| 47 | — | 232.0 ± 28.0 |
| 48 | — | 296.0 ± 56.0 |

*Given at a dose of 100 mg/kg.

(Benzbromarone) was administered subcutaneously to mice in an amount of 200 mg./kg. as a control or standard. The phenol red retention was found to be 184.2%.

The same test of uricosuric activity was applied to rats. The results are shown in Table II.

TABLE II

| Uricosuric Activity by Phenol Red Method | |
| --- | --- |
| Compound No. | Phenol Red Retention % in Rats 100 mg/kg (p.o.) |
| 3 | 194.6 ± 29.7 |
| 22 | 217.2 ± 17.2 |
| 25 | 208.1 ± 27.0 |
| 35 | 269.0 ± 31.0 |
| 39 | 175.7 ± 21.6 |
| control Benzbromarone | 163.9 ± 25.0 |

The following examples illustrate the preparation of compounds of the invention.

EXAMPLE 1

2-(2-ethyl-3-benzofuroyl)phenoxy-acetic acid.
(Compound 1)

Procedure A.—To an ice cooled solution of 2-ethyl benzofuran 5.0 g and 5.9 g of o-anisoyl chloride dissolved in 20 ml benzene were added 4.1 ml of SnCl$_2$ dropwise; the reaction mixture was stirred for 3 hours at room temperature. Then it was poured into water, 30 g, containing 5 ml of conc. HCl. The benzene layer was separated and the solution was extracted with benzene again. The combined benzene layer was washed with a 5% NaHCO$_3$ solution and then with water. After drying and removal of benzene under reduced pressure, the yellowish oil, 2-ethyl-3-(o-anisoyl) benzofuran was obtained. Pyridine-HCl was prepared by the introduction of dried HCl gas to 4.75 g of pyridine and a 50 ml of benzene solution, and then by removing benzene twice.

To the pyridine-HCl thus obtained, were added 2-ethyl-3-(o-anisoyl) benzofuran, 5.61 g, and then the reaction mixture was refluxed slowly at a temperature 200°-220° C. for 3 hrs. After cooling at room temperature, the solidified product was dissolved in a solution of 10% HCl with benzene, 40 ml. The benzene layer was separated and the water layer was extracted again with 20 ml benzene. The combined benzene layer was made alkaline with a 10 % NaOH solution.

The separated aqueous layer was washed with a small portion of benzene and then acidified with 10 % of HCl, extracted with 20 ml of benzene three times. After washing with water, drying and removal of the benzene, a brown viscous residue was obtained, which was then solidified after overnight standing. The compound could be recrystallized from benzene.

Procedure B—To a solution of 13 ml of DMF in which NaH (55 %) 0.53 g was suspended, was added dropwise the product of the first step,2-ethyl-3-(2-hydroxybenzoyl) benzofuran, 1.33 g dissolved in DMF, 4 ml. After 10 minutes stirring at room temperature, monochloroacetic acid (0.57 g) was added carefully. The mixture was stirred for 6 hours at 100° C. After cooling, the reaction mixture was poured into 100 ml of ice-water, acidified with 10 % HCl and then subjected to ether extraction. The ether layer was washed with water and dried. After removal of the ether in vacuo, a crystal residue was obtained and recrystallized from isopropyl alcohol.

m.p.: 173°-176° C., ir spectrum : 3400, 3030, 1735 cm$^{-1}$, M.S. (m/e): 324 (M+).

EXAMPLE 2

3-(2-ethyl-3-benzofuroyl) phenoxyacetic acid.
(Compound 2)

By the same operation as Example 1 and starting from m-anisoyl chloride instead of o-anisoyl chloride, the compound 2 was obtained.

m.p.: 105°-108° C. (decomp.), ir : 3400, 3060, 1745, 1650 cm$^{-1}$ M.S (m/e) : 324 (M+).

EXAMPLE 3

4-(2-ethyl-3-benzofuroyl) phenoxyacetic acid.
(Compound 3)

By the same operation as Example 1 and starting from p-anisoyl chloride via an intermediate 2-ethyl 3-(4-hydroxybenzoyl)benzofuran, the compound 3 was obtained.

m.p.: 172–175 °C., ir spectrum : 3400, 3030, 1740, 1640, 1600 cm$^{-1}$, M.S. (m/e) : 324 (M+).

EXAMPLE 4

4-(2-ethyl-3-benzofuroyl)phenoxypropionic acid (Compound 4)

From the intermediate in

EXAMPLE 3 by reacting with 3-chloropropionic acid in the same manner as the Procedure B of Example 1, the compound 4 (liquid) was obtained.

ir spectrum: 3050, 1715, 1640, 1250 cm$^{-1}$; MS(m/e) : 338(M+).

EXAMPLE 5

4-(2-ethyl-3-benzofuroyl)phenoxy-2-methylacetic acid. (Compound 5)

By using 2-bromopropionic acid instead of 3-chloropropionic acid in Example 4, the compound 5 was obtained.

m.p.: 182°–184° C. ir: 3420, 2960, 1735, 1605 cm$^{-1}$; M.S. (m/e) : 338 (M+).

EXAMPLE 6 ethyl 4-(2-ethyl-3-benzofuroyl)phenoxyacetate (Compound 6)

From the intermediate in

EXAMPLE 3 by reacting with ethyl bromoacetate in the same manner as procedure B of Example 1, the compound 6 (liquid) was obtained.

ir spectrum: 3050, 1760, 1645, 1200 cm$^{-1}$; M.S.(m/e) : 352(M+).

EXAMPLE 7

4-(2-ethyl-3-benzofuroyl)phenoxyacetamide. (Compound 7)

According to the Procedure B of Example 1, the intermediate of the Example 3 was reacted with methyl chloroacetate. The resulting product methyl 4-(2-ethylbenzofuroyl) phenoxyacetate (Compound 11) was treated with concentrated ammonia water 28%) 100 ml and was stirred under ice-cooled condition for three hours. The white powder thus obtained, after drying was recrystallized from methanol.

m.p.: 187°–188° C., ir : 3410, 3060, 1690, 1650 cm$^{-1}$ M.S.(m/e) : 328 (M+).

EXAMPLE 8

4-(2-ethyl-3-benzofuroyl)phenoxyacetohydroxamide (Compound 8)

The compound 11 (20.3 g) was addded to a hydroxyaminemethanol solution, which was prepared from hydroxyamine hydrochloride, 4.17 g, with the addition of KOH 7.29 g in MeOH 25 ml. After stirring for 3 hrs. in an ice-cooled bath and letting it stand oveunight at room temperature, water was added to make it 350 ml in all. After filtration, the water layer was washed with a small amount of ether. The water layer Was then warmed up on boiling water for 15 minutes. Crystals formed by cooling at room temperature were collected and washed with cooled water, and recrystallized from methanol and water.

m.p.: 152°–154 °C., ir spectrum: 3280, 2930, 1680, 1630 cm$^{-1}$ M S.(m/e): 339(M+).

EXAMPLE 9

Methyl 4-(2-ethyl-3-benzofuroyl)phenoxyacetoglycinate (Compound 9)

0.995 g of Compound 3 and 0.439 g of glycine methyl ester hydrochloride were suspended in 15 ml of DMF and to this mixture, was added 0.75 ml of DPPA dropwise during stirring at 0° C. Then 0.91 ml of triethylamine in a 5 ml DMF solution was added dropwise. The stirring was continued for three hours and the mixture was allowed to stand overnight at room temperature. The reaction mixture was poured into 100 ml of icewater and was extracted with ethyl acetate. The yellowish powder, which was obtained after washing with a 5 % NaHCO$_3$ solution and water, drying and evaporation of the ethyl acetate layer, was recrystallized from 5 ml of ethyl acetate.

m.p.: 135°–137 °C., ir spectrum: 3290, 1730, 1660, 1610, 1540 cm$^{-1}$, M.S.(m/e): 395(M+).

EXAMPLE 10

5-(2-Ethyl-3-benzofuroyl)phenoxyacetoglycinamide (Compound 10)

To concentrsted ammonia water (28%) 10 ml, were added 620 mg of compound 9 and the mixture was stirred for 8 hours at room temperature. The reaction mixture was extracted with 60 ml of ethyl acetate after the addition of water (20 ml) and NaCl (2 g). The liquid substance obtained after washing, drying and concentration of the ethyl acetate layer, was applied to Kiesel—Gel 40 (trade name) packed column for purification purposes. (developer: CHCl$_3$: MeOH=10:1)

m.p.: 139°–142° C. (decomp.), ir: 3350, 1700, 1660, M.S.(m/e) : 380(M+).

EXAMPLE 11

Methyl 4-(2-ethyl-3-benzofuroyl)phenoxyacetate (Compound 11)

Compound 11 was the intermediate of Example 7.

m.p.: 72°–74° C., ir: 2950, 1765, 1640, 1600 cm$^{-1}$ M.S (m/e): 338(M+).

EXAMPLE 12

2-methylene-4-oxo-4-(2-ethyl-3-benzofuranyl)butyric acid (Compound 21)

At room temperature, 8.0 g of anhydrous aluminum chloride and 3.59 g of itaconic acid anhydride were dissolved in distilled tetrachloroethane, 20 mL with virgorous agitation. Then the solution was cooled on an ice-water bath and to this, 2-ethybenzofuran, 4.39 g, dissolved in 10 ml of tetrachloroethane were added dropwise. After three hours stirring in an ice-water bath followed by 12 hrs. stirring at room temperature, the reaction mixture was poured into ice-water, 80 g, containing 20 ml of HCl and extracted with ethyl acetate. The ethyl acetate layer was extracted with 50 ml of a 10% NaCO$_3$ solution and then the aqueous layer was acidified with 10% HCl again and extracted with ethyl acetate. After washing with water, drying and removal of the solvent, the resulting viscous oily substance was extracted with ligroin (20 ml ×3). Needle-like crystals were obtained after overnight standing at room temperature.

m.p.: 160°–162° C. ir: 3400, 2970, 1710, 1680 cm$^{-1}$ M.S.(m/e): 258(M+).

EXAMPLE 13

2-Methylene-4-oxo-4-(2-ethyl-3-benzo-furanyl)butyric acid (Compound 21)

A suspension of 8.0 g of anhydrous aluminum chloride and 3.59 g of itaconic acid anhydride in dried tetrachloroethane was stirred for one hour at room temperature. To this solution, 4.39 g of 2-ethylbenzofuran dissolved in 10 ml of tetrachloroethane was added dropwise under cooling by ice-water. And then stirring was continued for 3 hrs. in ice-water and for 12 hrs. at room temperature. The reaction mixture was poured into the mixture of 80 g of ice and 20 ml of conc. HCl, then extracted with ethylacetate (50 ml). After washed with water, the solvent layer was made alkaline with 10% NaCO₃ solution. The water layer was acidified with 10% HCl again and then was extracted with ethylacetate. The brown viscous residue obtained after washing, drying and removal of ethyl acetate layer, was extracted with ligroin. After standing overnight, the needle-like crystals were obtained.

m.p.: 160°–162° C., ir: 3400, 2970, 1710, 1680 cm$^{-1}$
M.S.(m/e): 258 (M+).

All other compounds synthesized by a procedure pursuant to the aforesaid examples are summarized as follows.

Compound 13: Ethyl 4-(2-ethyl-3-hydroxymethylbenz:ofuranyl) phenoxyacetate
m.p.: 96°–97° C.
ir. spectrum: 3490, 2960, 1735, 1510 cm$^{-1}$.
M.S. (m/e): 354(M+).

Compound 14: Ethyl 4-(2 ethyl-3-ethoxymethylbenzofuranyl phenoxyacetate
ir.: 3050, 1760, 1640, 1610, 1510 cm$^{-1}$.
M S. (m/e): 382(M+).

Compound 15: Butyl 4-(2-ethyl-3-butoxymethylbenzofuranyl) phenoxyacetate
ir.: 3050, 1760, 1610, 1510, 1300 cm$^{-1}$.
M.S. (m/e): 438(M+).

Compound 16: 2-methyl-3-(4-hydroxybenzoyl)benzofuran
m.p.: 145°–147° C.
ir. 3100, 1620, 1580, 1560, 1390 cm$^{-1}$.
M.S. (m/e): 253(M++1), 252(M+).

Compound 17: Ethyl 4-(2-methy-1-3-benzofuroyl)phenoxyacetate
m.p.: 80°–81° C.
ir. 2980, 1735, 1630, 1600 cm$^{-1}$.
M.S.(m/e): 338(M+).

Compound 18 4-(2-methyl-3-benzofuroyl)phenoxyacetic acid
m.p.: 203°–204° C.
ir: 3420, 3025, 1735, 1635, 1600 cm$^{-1}$.
M.S.(m/e): 310(M+).

Compound 19: 2-ethyl-benzofuranyl-3-chloro-4-hydroxyphenyl ketone
ir: 3300, 1625, 1595, 1560 cm$^{-1}$.
M.S.(m/e): 301(M++1), 300(M+).

Compound 20: Ethyl 2-chloro-4-(2-ethyl-3-benzofuroyl) phenoxyacetate
ir: 3050 760, 1645, 1595 cm$^{-1}$.
M.S.(m/e): 387(M+1), 386(M+).

Compound 22: 2-chloro-4(2-ethyl-3-benzofuroyl)phenoxyacetate acid
m.p.: 156°–159° C.
ir: 3420, 3050, 2960, 1740 cm$^{-1}$.
M.S.(m/e): 360(M++1), 358(M+).

Compound 23: 2-ethyl-3-benzofuroyl 3-methyl-4-hydroxyphenyl ketone
m.p.: 115°–117° C.
ir: 3350, 3030, 2960, 1630, 1570 cm$^{-1}$.
M.S. (m/e): 280(M+).

Compound 24: Ethyl 2-methyl-4-(2-ethyl-3-benzofuroyl phenoxyacetate
ir: 3060, 1760, 1645, 1600, 1505 cm$^{-1}$.
M.S.(m/e): 366 (M+).

Compound 25: 2-methyl-4-(2-ethyl-3-benzofuroyl)-phenoxyacetic acid
m.p.: 150°–152 ° C.
ir: 3400, 3040, 2970, 1740, cm$^{-1}$.
M.S.(m/e): 338(M+).

Compound 26: 2-ethyl-3-benzofuranyl-3-nitro-4-hydroxyphenyl ketone
ir: 3220, 3080, 2950, 1620 cm$^{-1}$.
M.S. (m/e): 311(M+).

Compound 27: Ethyl 2-nitro-4-(2-ethyl-3-benzofuroyl) phenoxyacetate
ir: 3070, 1755, 1650, 1610, 1540 cm$^{-1}$.
M.S (m/e): 397(M+).

Compound 28: 4-(2-ethyl-3-hydroxymethylbenzofuranyl) phenoxyacetamide
ir: 3430, 3150, 1690, 1505 cm$^{-1}$.
M.S.(m/e):325(M+).

Compound 29: 2-ethyl-3-(4-hydroxybenzoyl)thianaphthene
m.p.: 167°–169 ° C.
ir: 3210, 1620, 1585, 1510, 1335 cm$^{-1}$.
M.S.(m/e): 282(M+).

Compound 30: Ethyl 4-(2-ethyl-3-benzothenoyl)-phenoxy acetate
m.p.: 109°–111° C.
ir: 2950, 1740, 1630, 1600, 1510 cm$^{-1}$.
M.S.(m/e): 368 (M+).

Compound 31: 4-(2-ethyl-3-benzothenoyl)phenoxyacetic acid
m.p.: 169°–170 ° C.
ir: 3400, 3050, 2960, 1735 cm$^{-1}$.
M.S.(m/e): 340(M+).

Compound 32: 2-ethyl-3-(2,3-dimethyl-4-hydroxybenzoyl) benzofuran
m.p.: 135°–136 ° C.
ir: 3350, 2950, 1620, 1570, 1450 cm$^{-1}$.
M.S.(m/e): 294(M+).

Compound 33: Methyl 2,3-dimethyl-4-(2-ethyl-3-benzofuroyl) phenoxyacetate
m.p.: 93°–94 ° C.
ir: 1750, 1620, 1550, 1450 cm$^{-1}$.
M.S.(m/e): 366(M+).

Compound 34: Ethyl 2,3-dimethyl-4-(2-ethyl-3-benzofuroyl) phenoxyacetate
m.p.: 85°–86° C.
M.S.(m/e): 380(M+).

Compound 35: 2,3,-dimethyl-4-(2-ethyl 3-benzofuroyl) phenoxyacetic acid
m.p.: 142°–144° C.
ir: 3040, 2910, 1720, 1630 cm$^{-1}$.
M.S.(m/e): 352(M+).

Compound 36: 2-ethyl-3-(2,5-dimethyl-4-hydroxybenzoyl) benzofuran
m.p.: 163°–164° C.
ir: 3150, 1600, 1550, 1450 cm$^{-1}$.
M.S.(m/e): 294(M+) 265(B).

Compound 37: Methyl 2,5-dimethyl-4-(2-ethyl-3-benzofuroyl)phenoxyacetate ir: 2900, 1750, 1640, 1560, 1450 cm$^{-1}$.
M.S.(m/e): 366 (M+).

Compound 38: Ethyl 2,5-dimethyl-4-(2-ethyl-3-benzofuroyl) phenoxyacetate
ir: 2950, 1750, 1650, 1460 cm$^{-1}$.
M.S.(m/e): 380(M+), 352(B).

Compound 39: 2,5-dimethyl-4-(2-methyl-3-benzofuroyl) phenoxyacetic acid
m.p.: 140°–141 ° C.
ir: 3040, 1740, 1640, 1570 cm$^{-1}$.
M.S.(m/e): 352(M+), 323(B).

Compound 40: 2-ethyl-3-(3,5-dimethyl-4-hydroxybenzoyl) benzofuran
m.p.: 124°–126° C.
ir: 3400, 1630, 1590, 1450 cm$^{-1}$.
M.S.(m/e): 294(M+, B).

Compound 41: Ethyl 2,6-dimethyl-4-(2-ethyl-3-benzofuroyl) phenoxyacetate
ir: 2970, 1760, 1650, 1455 cm$^{-1}$.
M.S (m/e): 380(M+B).

Compound 42: 3,6-dimethyl-4-(2-ethyl-3-benzofuroyl) phenoxyacetic acid
m.p.: 169°–171° C.
ir: 3020, 1725, 1640, 1570 cm$^{-1}$.
M.S. (m/e): 352(M+), 337(B).

EXAMPLE 14

5-[4-(2-ethyl-3-benzofuroyl) phenoxymethyl]tetrazole (Compound 43)

To an ice-water cooled suspension of NaH (0.18 g) in dry DMF (5 ml), is added a solution of a 2-ethyl-3-(4-hydroxybenzoyl) benzofuran, 100 g, in dry DMF 12 ml dropwise. After stirring for about 15 minutes running, chloroacetonitrile (0.24ml) is added and heated up to 100° C. for 3 hours. After cooling to room temperature, the reaction mixture is poured over ice-water 100 ml and submitted to extraction by ethyl acetate. The solvent layer is washed by 10% NaOH solution and washed by NaCl solution and then dried by Na$_2$CO$_3$. Removing the solvent from the resulting solution gives a yellowish oily substance, that is 4-(2-ethyl-3-benzofuroyl)phenoxyacetonitrile. The obtained substance, in an amount of 1.05 g is dissolved in 15 ml of THF under an N$_2$ gas stream. To this solution, aluminum chloride anhydride powder, 0.46 g,and then sodium azide,0.98,are added and heated up to reflux for 24 hours. The reaction mixture is cooled by ice water and 10% HCl is added dropwise to make the solution acidic. After removal of THF, water is added and extracted by ethyl acetate (30 ml×2). The organic layer is washed by NaCl solution and dried over NaCO$_3$. A solid substance obtained after removal of the organic solvent is recrystallized from CH$_2$Cl$_2$.
m.p.: 173°–175° C.
ir: 3860, 1630, 1600, 1255 cm$^{-1}$.
M.S.(m/e): 348(M+), 305, 265(B), 250.

Other compounds from No. 44 to No. 48 are obtained from corresponding phenol of general formula (V) in the same procedure as Example 14.

Compound 44: 5-[2-chloro-4-(2-ethyl-3-benzofuroyl) phenoxymethyl]tetrazole
m.p.: 182°–185° C.
ir: 3050, 1620, 1590, 1555 cm$^{-1}$.
M.S.(m/e): 384 (M+ +2) 382(M+), 338, 297.

Compound 45: 5-[2-methyl-4-(2-ethyl-3-benzofuroyl) phenoxymethyl]tetrazole
m.p.: 173°–176° C.

ir: 3050, 1635, 1795, 1500 cm$^{-1}$.
M.S.(m/e): 362(M+), 319, 304, 280, 278(B).

Compound 46: 5-[2,3-dimethyl-4-(2-ethyl-3-benzofuroyl) phenoxymethyl]tetrazole
m.p.: 161°–163° C.
ir: 3000, 1630, 1560, 1450 cm$^{-1}$.
M.S.(m/e): 333(M+), 329, 305, 279, 265.

Compound 47: 5-[2,5-dimethyl-4-(2-ethyl-3-benzofuroyl) phenoxymethyl]tetrazole
m.p.: 155°–157° C.
ir: 3000, 1630, 1570, 1450, 755 cm$^{-1}$.
M.S.(m/e): 376(M+), 347, 333, 318.

Compound 48: 5-[2,6-dimethyl-4-(2-ethyl-3-benzofuroyl) phenoxymethyl]tetrazole
m.p.: 178°–179° C.
ir: 3025, 1620, 1585, 1480 cm$^{-1}$.
M.S.(m/e): 376 (M+), 333, 293, 279, 265.

What we desire to claim and protect by Letter Patent is:

1. A compound of the formula

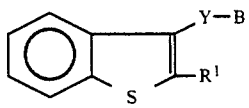

wherein:
$R^1$ is lower alkyl;
$R^2$ is hydrogen or lower alkyl
Y is carbonyl,
B is

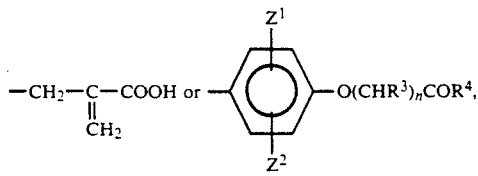

wherein
$R^4$ is a hydroxy, alkoxy, amino, hydroxylamino, —NHCH$_2$CONH$_2$—, or NHCH$_2$COOR$^5$ group, wherein $R^5$ is a lower alkyl group,
$Z^1$ and $Z^2$ are each selected from a hydrogen atom or a lower alkyl group, and
n is an integer of 1 or 2 and
pharmaceutically acceptable salts thereof.

2. The compound according to claim 1 wherein B is

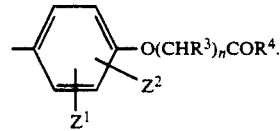

3. The compound according to claim 2 wherein $R^4$ is an amino or hydroxylamino group.

4. The compound according to claim 2 wherein $R^4$ is —NHCH$_2$CONH$_2$ or —NHCH$_2$COOH$^5$, wherein $R^5$ is a lower alkyl group.

5. The compound according to claim 2 wherein $Z^1$ and $Z^2$ are each a hydrogen atom.

6. The compound according to claim 1, which is 4-(2-ethyl-3-benzothenoyl)phenoxyacetic acid.

7. The compound according to claim 1, wherein B is
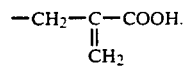
8. A diuretic composition with uricosuric activity comprising a pharmaceutically acceptable carrier and, as an active ingredient, a compound defined in claim 1 in an amount effective to inhibit hyperuricemia.
* * * * *